United States Patent [19]

McMorris et al.

[11] 3,973,194

[45] Aug. 3, 1976

[54] PARTICLE COUNTER

[75] Inventors: Daniel W. McMorris, Redondo Beach; William J. Skidmore, III, Costa Mesa, both of Calif.

[73] Assignee: Becton, Dickinson and Company, East Rutherford, N.J.

[22] Filed: Aug. 7, 1972

[21] Appl. No.: 278,422

[52] U.S. Cl. .......................................... 324/71 CP
[51] Int. Cl.² ........................................... G01N 27/00
[58] Field of Search .................... 324/71 CD, 771 R; 235/92 PC; 250/118; 307/235; 328/116, 117, 135

[56] References Cited
UNITED STATES PATENTS

| | | | |
|---|---|---|---|
| 2,656,508 | 10/1953 | Coulter | 324/71 CP |
| 2,719,287 | 9/1955 | Bartlett | 340/239 |
| 3,231,815 | 1/1966 | Spencer | 324/71 CP X |
| 3,271,672 | 9/1966 | Henderson | 324/71 CP |
| 3,393,319 | 7/1968 | Randall et al. | 250/218 X |
| 3,473,010 | 10/1969 | Bloomfield et al. | 324/71 CP X |
| 3,676,783 | 7/1972 | Kinbara et al. | 307/235 R X |
| 3,733,548 | 5/1973 | Coulter et al. | 324/71 CP |

Primary Examiner—John K. Corbin
Assistant Examiner—Rolf Hille
Attorney, Agent, or Firm—Kane, Dalsimer, Kane, Sullivan and Kurucz

[57] ABSTRACT

A fluid containing disbursed particles is pumped through an aperture which has a pair of electrodes mounted on each side of said aperture. The pair of electrodes is excited by an rf signal which is modulated by the particles passing through said aperture. The rf signal is then detected, filtered and amplified to provide pulses corresponding to the particles passing through the aperture. Means for charging a capacitor at a known rate during a portion of each pulse that exceeds a predetermined threshold level to develop a voltage on the capacitor corresponding to the number of particles per unit volume of the fluid medium, said voltage being independent of flow rate and the volume of fluid passed through the aperture. An alarm is provided to warn of a possible clogged aperture and a pulse width limiter is provided to prevent erroneous charging of the capacitor if a bubble passes through the aperture.

23 Claims, 6 Drawing Figures

PARTICLE COUNTER

BACKGROUND OF THE INVENTION

1. Field of the Invention

The present invention relates to counters for counting particles suspended in a fluid medium and more particularly to counters using pulse width integration for measuring paticles per unit volume of fluid medium.

2. Description of the Prior Art

The prior art in the broad field of particle counting may be described by considering the more limited field of blood cell counting. Heretofore, blood cell counting was accomplished in three distinctly different ways. Firstly, a sample of diluted blood was placed under a microscope and the blood cells were individually counted to determine the blood cell count. Secondly, a more sophisticated blood cell counting system utilized optics and photoelectric cells to provide a count of the number of blood cells passing through a light beam. Thirdly, pure electronic blood cell counters were utilized wherein changes in conductivity of a diluted blood sample were sensed to provide an output corresponding to the number of blood cells in the sample.

Some of the less sophisticated pure electronic blood cell counters merely applied a signal across a volume of diluted blood and utilized the voltage developed across the blood sample as an indication of the number of blood cells present. This type of device is inaccurate and did not prove satisfactory.

A more sophisticated type of pure electronic blood cell counter was developed wherein a known volume of diluted blood was drawn through an aperture and a DC electric signal was applied to electrodes positioned at each side of the aperture to develop a voltage corresponding to the instantaneous conductivity of the blood sample passing through the aperture. Since blood cells have extremely low conductivity as compared to the diluent in which they are diluted, each time a blood cell passed between the electrodes, the voltage between the electrodes would increase and provide a pulse output. When the pulses exceeded a predetermined threshold level, a blood cell was counted.

The DC type devices suffered from unique problems relating to electrode stability. Base line instability occurred because of bubble formation and the devices were sensitive to polarization potentials.

To provide a more accurate blood cell count, some of the devices of the prior art volumetrically controlled the amount of blood sample passed through the aperture and initiated and stopped counting based on volume measurements. These devices were expensive and subject to errors because of the difficulty in making accurate volume measurements.

Another problem encountered by the aperture type systems of the prior art was the correction for blood cell coincidence. The devices of the prior art generated a single pulse output for every detected blood cell passing through the aperture. However, when blood cells passed through the aperture in total or partial coincidence, only a single pulse would result and one cell would be counted. In order to correct for this error, the devices of the prior art provided correction tables so that a count of the total output pulses could be converted to a more accurate count by the addition of a statistically determined number of cells. As can be seen, such a system is subject to errors and cannot be said to provide an actual count of the blood cells passing through the aperture.

Another problem experienced with aperture type systems was the accumulation of lint and dust in the aperture, which caused the aperture to become clogged resulting in errors in the blood cell count. In order to detect aperture clogging, the devices of the prior art provided oscilloscopes to view a trace of the voltage generated across the aperture so that any abnormality could quickly be detected and a viewing screen was provided so that aperture could be continuously observed to determine if clogging was taking place.

The formation of bubbles around the aperture caused faulty blood cell counts in the prior art devices. Each time a bubble would pass through the aperture, an additional blood cell was counted thereby resulting in an inaccurate blood count.

Thus, the devices of the prior art required the use of correction tables and did not provide direct readings of the actual blood cell count. In addition, these devices were large and expensive, thereby making them impractical for use by individual doctors, veterinarians and small laboratories.

SUMMARY OF THE INVENTION

The present invention contemplates a particle counter that may also be used as a blood cell counter that provides practicing physicians, veterinarians and laboratories with a simple, reliable and accurate instrument for counting white and red blood cells. The instrument automates the tedious task of physically counting individual blood cells and uses integrated circuits and automatic compensation devices to provide a quick and accurate blood count.

The operational concept of the counter is based upon the difference in electrical conductivity between particles to be counted and the fluid in which the particles are suspended. When used as a blood cell counter, the device depends on the difference of conductivity between blood cells and the diluent used to prepare blood samples. The diluted blood sample is drawn through an aperture of known size so that as individual blood cells pass through the aperture, the resistance across the aperture abruptly increases. An rf signal is applied to electrodes on each side of the aperture so that the signal is modulated by the variation of the resistance between the electrodes as blood cells pass through the aperture. The modulated rf signal is capacitively coupled to a signal detector where it is demodulated to provide pulses corresponding to the blood cells passing through the aperture. The rf frequency is greatly attenuated by passing the signals through a low-pass filter after which the pulses are amplified and shaped.

The pulse signals are then directed to three detectors, the outputs of which control an integrator control flip flop. The first detector detects if a pulse exceeds a specified threshold level. The second detector, detects the pulse peak and the third detector determines when the trailing edge of the pulse is at a level equal to one half of the level of the pulse peak. When the threshold level has been exceeded by a pulse and the pulse peak is detected, the integrator control flip flop is driven to a set state, if other conditions also prevail. The flip flop remains in the set state until the third detector detects the half-pulse peak level at which time the integrator control flip flop is driven to a reset state. When the integrator control flip flop is in the set state, an output signal is provided to a gate that allows a storage capacitor to be charged from a constant current source. The capacitor charges at a constant rate during the time between the pulse peak and the one-half peak level of the trailing edge of the pulse. The capacitor retains this charge and accumulates successive charges from subsequent pulses.

A timer circuit inhibits the integrator control flip flop from entering the set state except during a precisely controlled pulse count period during which the integrator control flip flop is enable and is driven to a set state upon detection of a pulse peak that exceeds the threshold level. The integrator control flip flop is reset by the third detector when it detects the half-pulse peak level of the trailing edge. During the pulse count period, the flip flop alternately changes state as subsequent pulse peaks and half-pulse peak levels are detected. Thus, a series of charges are supplied to the storage capacitor which accumulates the charges to develop an analog voltage corresponding to the number of blood cells passing through the aperture. After the count period, the timer circuit again inhibits the integrator control flip flop preventing it from being driven to a set state. The analog voltage stored on the capacitor is connected to a meter which is directly calibrated in cells per cubic millimeter.

A clog detector and alarm are provided to warn of the presence of foreign matter in the aperture so that a particular blood count may be disregarded if a clog should develop during a particular count period. A pulse width limiter is also provided to limit the period of time during which the integrator control flip flop may be maintained in the set state. This limiter prevents the integrator control flip flop from remaining in the set state during the entire period during which a bubble passes through the aperture. Bubbles take an exceedingly long time, relatively speaking, to pass through the aperture and therefore, introduce considerable errors in the blood cell count unless limiting means are provided.

The instrument inherently compensates for coincidence of blood cells that pass through the aperture at one time. If blood cells are partially coincident a longer, or wider pulse will result as they pass through the aperture. Because of the wider pulse, the capacitor will charge for a longer period of time, thereby accounting for the partially coincident cells. Truly coincident cells will cause a pulse having a normal width and only one cell will be counted; however, the meter has a scale that is calibrated to compensate for the truly coincident cells on a statistical basis so that number of cells read from the meter is equal to the number of cells actually passing through the aperture within specified tolerances.

The instrument is flow independent because as the flow rate increases, the pulse width decreases charging the capacitor a correspondingly shorter time; however, the number of cells passing through the aperture increases resulting in the same voltage being developed across the capacitor over a like period of time. Thus, the system is self-compensating for variations in flow rate. It is essential that the count period be precisely repeatable so that once the instrument is calibrated to a known assay sample subsequent blood counts will be accurate despite variations in sample flow rate.

By the unique use of dynamically controlled detecting circuits for controlling the integration control flip flop, small pulses that barely exceed the threshold level are not lost in the integrating process. If the integration control flip flop was set only during the time that a pulse exceeded a specified threshold level, the charge received by the capacitor would vary greatly between pulses so that a very small charge would be received for small pulses and a large charge for large pulses thereby making the capacitor voltage dependent upon pulse size rather than the number of blood cells passing through the aperture. By the use of dynamic threshold circuitry, it is assured that even the smallest of pulses that barely exceed the threshold level will contribute a substantial charge to the capacitor.

The invention also contemplates an on-line blood cell counter that provides a continuous output reading of the blood count of the blood being passed through the apreture at any given time. In such a device, the count period is not utilized but the integrating capacitor is provided with a discharge path for continuous controlled discharging of the capacitor so that the instantaneous voltage on the capacitor corresponds to the blood count of the blood passing through the apreture.

The main objective of the present invention is to provide a blood cell counter that is not dependent upon volume measurement.

Another objective of the present invention is to provide a blood cell counter that is less expensive than those heretofore provided so that it will be available for use in doctors' offices and in small laboratories.

Another objective of the present invention is to provide a blood cell counter that is of smaller size than those heretofore provided.

Another objective of the present invention is to provide a blood cell counter having automatic cell coincidence compensation.

Another objective of the present invention is to provide an aperture type blood cell counter that is not dependent upon flow rate of the sample through the aperture or the sample volume.

Another objective of the present invention is to provide an aperture type blood cell counter using an AC signal to detect the blood cells.

Another objective of the present invention is to provide a blood cell counter having an analog output corresponding to the number of blood cells per cubic millimeter.

The foregoing objectives and advantages of the invention will appear more fully hereinafter from a consideration of the detailed description which follows, taken together with the accompanying drawings, wherein two embodiments of the invention are illustrated by way of example. It is to be expressly understood, however, that the drawings are for illustrative purposes only and are not to be considered as defining the limits of the invention.

DESCRIPTION OF THE INVENTION

The present invention pertains to devices for counting particles suspended in a fluid medium, wherein the medium and the particles have substantially different conductivities. The invention will be described as a blood cell counter, but it is to be understood that it could be used for counting other types of particles, such as dust or pollution.

Figure 1:
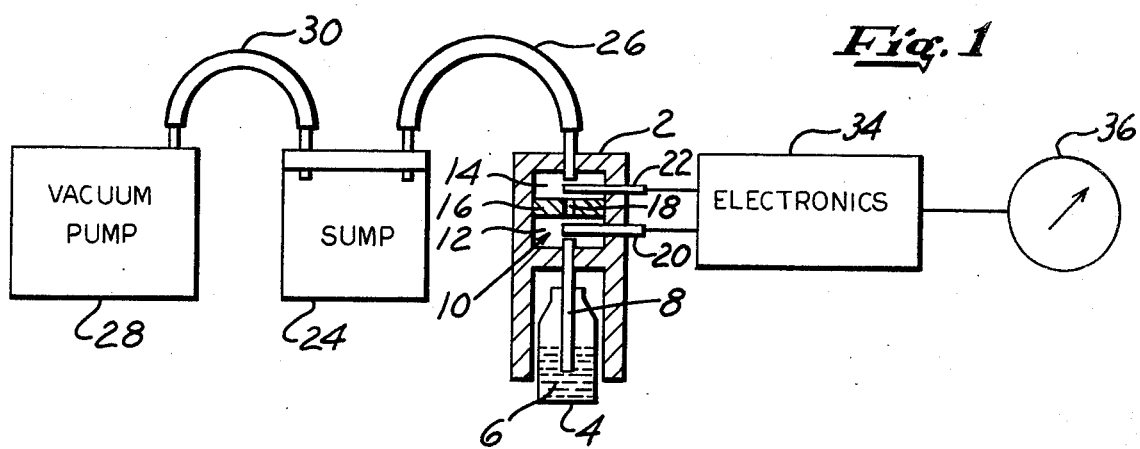
FIG. 1 is a diagram illustrating the system of the present invention.

Referring to FIG. 1, there is shown a diagrammatic representation of the system of the present invention. An electrode housing 2 receives a reservoir bottle 4 containing a diluted blood sample 6. A dip tube 8 extends downwardly from the electrode housing into the blood sample 6 contained in bottle 4. A cavity 10 is formed in the upper portion of the electrode housing and is divided into first and second chambers 12 and 14 by a partition 16 having an aperture 18 formed therein for connecting the first and second chambers. Dip tube 8 extends into the first chamber 12 of cavity 10 for connecting bottle 4 with chamber 12. Aperture 18 has a diameter of 90 microns, a diameter that was chosen because of its relationship to the size of a normal red blood cell. Electrodes 20 and 22 are mounted in the electrode housing 2 and extend into the first and second chambers respectively. The electrode housing and the partition 16 are formed of nonconductive material so that the electrodes remain electrically isolated from each other and do not short out through the electrode housing.

The invention is readily adaptable to an on-line operation where a continuous source of blood is provided in place of the reservoir bottle and the system provides a readout of the blood count of the blood passing through the instrument at that time. In such an embodiment a tube would be connected to the electrode housing and to dip tube 8 for supplying blood.

A sump bottle 24 has a hollow interior which is in communication with the second chamber 14 through a flexible tube 26. A vacuum pump 28 is pneumatically connected with the interior of sump bottle 24 through a flexible tube 30 for evacuating sump bottle 24 so that the pressure within the bottle is maintained below atmospheric pressure and the diluted blood sample 6 from the reservoir bottle 4 is drawn through dip tube 8 and into the first and second chambers 12 and 14 so as to establish a flow of blood sample through aperture 18.

Electronic circuitry 34 impresses an rf signal across the electrodes to develop a voltage across the electrodes dependent upon the instantaneous conductivity of the diluted blood sample passing through the aperture.

Blood cells have substantially lower conductivity than the diluent used for diluting the sample and therefore, abrupt voltage increases or pulses are generated each time a blood cell passes through the aparture. The electronic circuitry 34 senses the pulses and processes them to provide an output corresponding to the number of blood cells per cubic millimeter of blood sample passing through the aperture. This output is displayed on a readout device 36, such as a meter.

Figure 2:
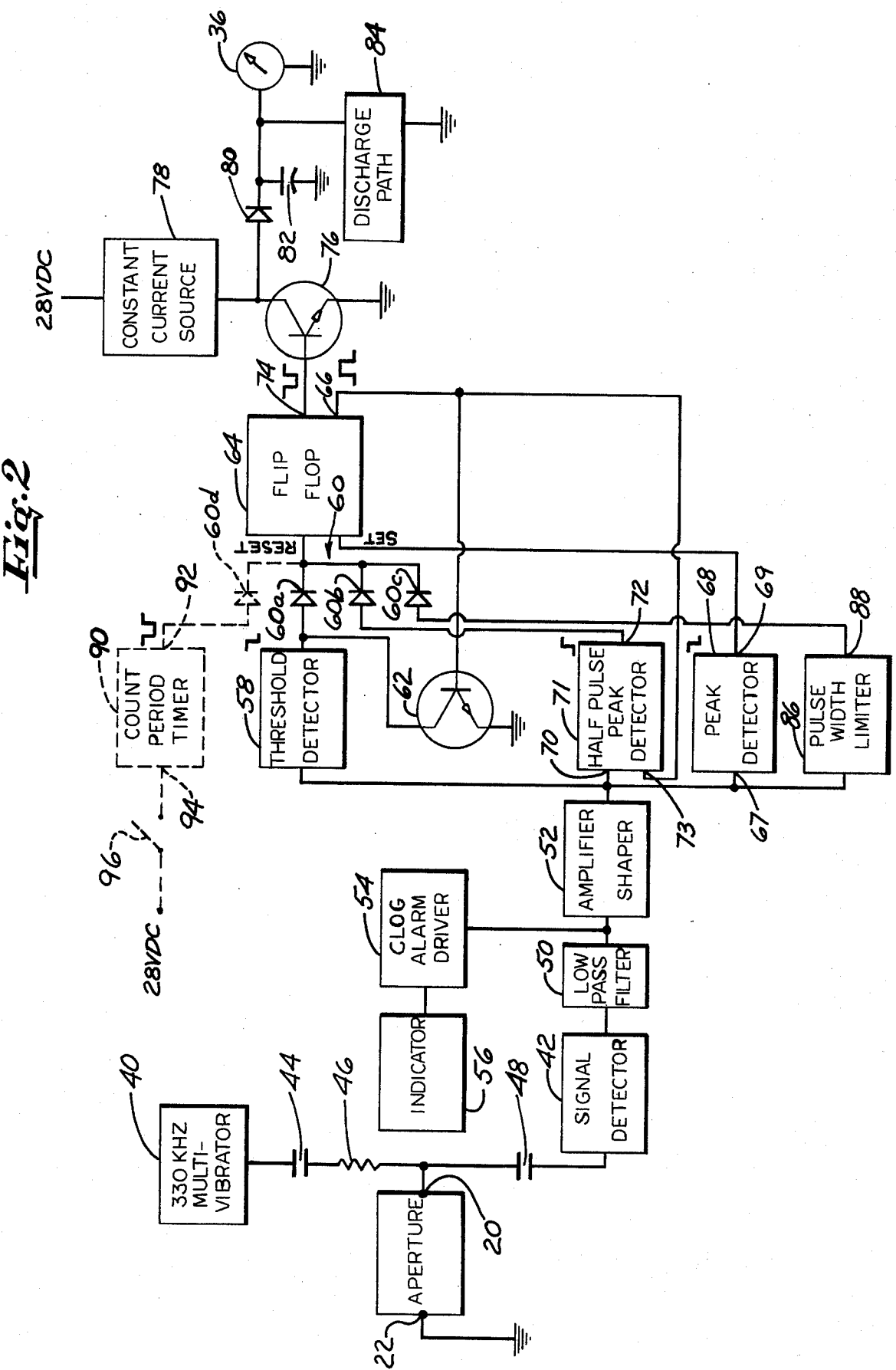
FIG. 2 is a schematic diagram showing the electrical system of the invention.

Referring to FIG. 2, there is shown a block diagram of the overall electronic circuitry of the instrument of the invention. A multivibrator 40 provides a square-wave output at a frequency of 330 KHz with a 20 volt peak output. The output of multivibrator 40 is connected to a signal detector 42 through a series circuit including a capacitor 44, a resistor 46 and a capacitor 48. The junction between resistor 46 and capacitor 48 is connected to electrode 20 of the electrode housing 2 while electrode 22 is connected to ground.

A voltage divider is formed by resistor 46 and the resistance across electrodes 20 and 22 so that the 330 KHz signal supplied by multivibrator 40 is modulated as the resistance across the electrodes changes when a blood cell passes through the aperture. Signal detector 42 functions as a demodulator and amplifier to provide a rectified signal to a low pass filter 50 which eliminates the rf component of the signal. The low pass filter is a six pole Butterworth Filter which passes frequencies below 33 KHz; therefore, the output of the low pass filter is a series of pulses corresponding to blood cells passing through the aperture. The filter output pulses are provided to an amplifier shaper 52 which provides output pulses having an amplitude of approximately 4 to 6 volts.

A clog alarm driver 54 is connected to the output of the low pass filter 50 and comprises a transistor biased to turn on at a predetermined voltage level. When the aperture becomes clogged, the resistance across the aperture increases so that the carrier signal increases in amplitude. The DC signal level from the low pass filter exceeds the predetermined voltage level of the clog alarm driver so that the driver provides an output which is connected to an indicator 56 for providing a visual indication or alarm indicating the aperture is clogged. The indicator may be a light bulb or its equivalent.

The output signal from the amplifier shaper 52 includes in addition to the blood cell pulses, noise and other low level pulses that do not represent blood cells. It is, therefore, desirable that the blood cell counter only count pulses above a certain threshold level. The output of the amplifier shaper is connected to an input of a threshold detector 58, which provides a negative or zero output level, which is defined as a logic 0, when a specified threshold voltage is exceeded. The threshold detector includes means for adjusting the threshold voltage level to an optimum value depending on the type of blood being counted, particularly if other than normal human blood or animal blood is being counted.

The output of the threshold detector is connected to a diode 60a of an OR gate 60 and also to the collector of a transistor 62. The output of OR gate 60 is connected to a reset input of a flip flop 64. When the threshold detector does not receive a signal exceeding the threshold, it provides a positive signal output which is defined as a logic 1 signal, to the OR gate. The logic 1 signal is passed to the reset input of flip flop 64 to hold flip flop 64 in its reset state, thereby disabling the effect of a signal at the set input on an output terminal 66 of the flip flop. The reset input of flip flop 64 has priority over the set input for controlling output 66.

The amplifier shaper output pulses are also directed to an input 67 of a peak detector 68 which has an output 69 that provides a signal that changes from a logic level 1 to a logic level 0 when the pulse peak occurs. Peak detector output 69 is connected to the set input of flip flop 64 which is responsive to a logic level 0 signal or a negative signal to set the flip flop causing it to change to the set state if the flip flop is not disabled by the presence of a logic level 1 signal at the reset input.

The output pulses from amplifier shaper 52, are also directed to an input 70 of a half-pulse peak detector 71 which has an output 72 that normally provides a logic level 0 output signal to a diode 60b of OR gate 60 but changes to a logic level 1 signal when the trailing edge of a pulse decreases to a level equal to one-half the pulse peak. Thus, a logic level 1 signal from the half-pulse peak detector 71 causes flip flop 64 to reset if it is in the set state.

It is to be understood that the half-pulse peak detector could be set to detect any other fraction of the peak voltage but that one-half was chosen for convenience.

Output 66 of flip flop 64 is connected to the base of transistor 62 and to a second input 73 of the half-pulse peak detector 71 for providing a logic level 1 signal thereto when said flip flop is in the set state and a logic level 0 signal when in the reset state. The second input 73 of half-pulse peak detector 71 is responsive to a logic level 0 signal for causing the half-pulse peak detector to store the pulses from the amplifier shaper and is responsive to a logic level 1 signal for holding the peal level of the pulse.

The presence of a logic level 1 signal on the base of transistor 62 causes it to turn on a clamp the output of the threshold detector 58 at a logic level 0 when the flip flop is in the set state. If a pulse peak should just slightly exceed the threshold level of threshold detetector 58, the threshold detector output will remain at a logic level 0 even when the trailing edge of the pulse declines below the threshold level and flip flop 64 will remain in the set state until the trailing edge of the pulse decreases to a value equal to one-half the pulse peak. Thus, the flip flop remains in a set state for a period of time depending upon the dynamically controlled threshold level of the half-pulse peak detector which is determined by peak level and width of each individual pulse. Without the clamping action of transistor 62, the threshold detector would reset the flip flop as soon as the trailing edge of the pulse declined to a level below the threshold level.

Flip flop 64 has an output 74 connected to the base of a transistor 76. Transistor 76 has an emitter connected to ground and a collector connected to output of a constant current source 78 which is powered by a 28 volt DC source. The output of the constant current source 78 is also connected to an anode of a diode 80 which has a cathode connected to one side of a storage capacitor 82, the other side of which is connected to ground. The cathode of diode 80 is also connected to the input of meter 36 and to ground through a discharge path 84.

In operation, when flip flop 64 is in the reset state, output 74 provides a logic level 1 signal causing transistor 76 to conduct, thereby shorting the current from the constant current source to ground and preventing capacitor 82 from charging. When a blood cell passes through the aperture, and a pulse peak is detected, flip flop 64 toggles to a set state and output 74 provides a logic level 0 signal causing transistor 76 to cut off so that the current from the constant current source is directed to capacitor 82 through diode 80 causing the capacitor to charge at a fixed rate and develop an analog voltage. Capacitor 82 accumulates the charges each time flip flop 64 is in the set state and the analog voltage developed corresponds to the total charge accumulated by the capacitor. Diode 80 prevents capacitor 82 from discharging through transistor 76 when it is turned on.

Discharge path 84 comprises a resistor for providing a controlled discharge of capacitor 82. In an embodiment of the invention designed for on-line operation, the resistor in discharge path 84 is selected so as to provide a slow discharge rate so that the analog voltage on the capacitor 82 will vary in corresponding relationship to the blood cell count of the blood sample passing through the aperture at that time. Meter 36 is responsive to the analog voltage to provide a readout that is calibrated to indicate blood cells per unit volume.

The output pulses from amplifier shaper 52 are also directed to a pulse width limiter 86 which provides a logic level 1 signal on an output 88 if the pulses from the amplifier shaper exceed a predetermined width such as 25 microseconds. Output 88 is connected to a diode 60c of OR gate 60 so that when a pulse has a width exceeding 25 microseconds the 1 level signal will reset flip flop 64 and prevent further charging of capacitor 82. When a bubble passes through the aperture, a wide pulse exceeding 25 microseconds results and without the previously mentioned pulse width limiter a large error would be introduced into the blood count reading. The pulse width limiter greatly reduces errors that would be introduced as a result of bubbles passing through the aperture.

Figure 3:
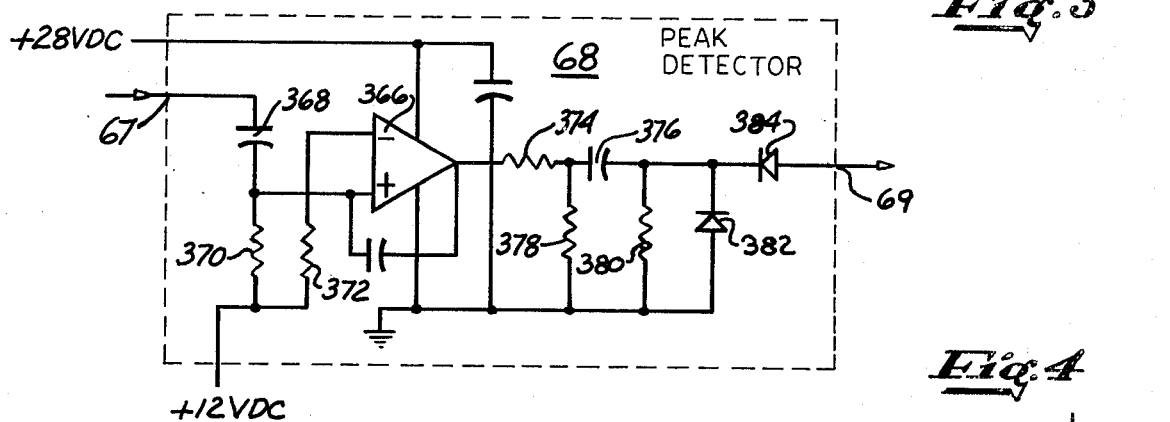
FIG. 3 is a schematic diagram of the peak detector circuit of FIG. 2.

Referring to FIG. 3, there is shown a circuit schematic for the peak detector 68 which provides a negative or logic level 0 output signal when a pulse peak if reached. The pulses received at input 67 are capacitively coupled to the input of an operational amplifier 366 by a capacitor 368. A 12 volt DC voltage is connected to the inputs of the operational amplifier by resistors 370 and 372. The amplifier output is connected to one end of a resistor 374 which has another end connected to a capacitor 376. The junction between resistor 374 and capacitor 376 is connected to ground by a resistor 378. A resistor 380 and a diode 382 are connected in parallel between ground and the other side of capacitor 376, the diode having its cathode connected to the capacitor. Another diode 384 has a cathode connected to the cathode of diode 382 and an anode connected to the output 69 of the detector.

Figure 4:
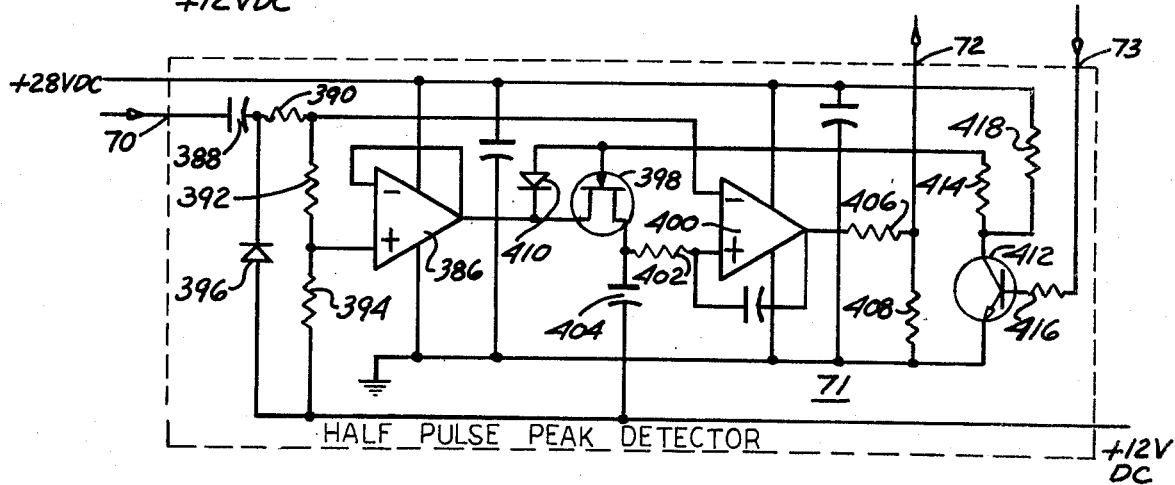
FIG. 4 is a schematic diagram of a half-pulse peak detector of FIG. 2.

Referring to FIG. 4, there is shown a schematic diagram for the half-pulse peak detector 71, which receives pulses at input 70 from amplifier shaper 52. The pulses are capacitively coupled to the input of an operational amplifier 386 through series connected capacitor 388, resistor 390 and resistor 392. A resistor 394 connects the input of amplifier 396 to a plus 12 volt DC source and a diode 396 is connected between the 12 volt source and the junction between capacitor 388 and resistor 390. The output of amplifier 386 is connected to the source element of a field effect transistor 398 which has a drain element connected to the non-inverting input of another operational amplifier 400 through a resistor 402. A capacitor 404 connects the drain element to the 12 volt DC source. The output of amplifier 400 is connected to ground through series connected resistors 406 and 408. The junction of resistors 406 and 408 are connected to output 72. The gate of field effect transistor 398 is connected to the source by a diode 410 having its cathode connected to the source. The gate is also connected to the collector of a transistor 412 through a resistor 414. The emitter of transistor 412 is connected to ground and the base is connected to output 66 of flip flop 64 through a resistor 416. A resistor 418 connects the collector of transistor 412 to a 28 volt DC source.

When flip flop 64 is in the reset state, the logic level 0 signal from output 66 causes transistor 412 to be turned off so that plus 28 volts is impressed on the gate of field effect transistor 398 causing it to be turned on. When transistor 398 is turned on, the output of amplifier 386 is connected to capacitor 404. Resistors 390, 392 and 394 form a voltage divider so that the junction of resistors 390 and 392 has a voltage equal to one-half of the input voltage and the junction between resistors 392 and 394 has a voltage equal to one-quarter of the input voltage. Thus, the non-inverting input of amplifier 386 receives a voltage equal to one-fourth the input voltage and provides at its output a voltage equal to one-fourth input voltage since the amplifier has a gain of one. The inverting input of amplifier 400 receives a voltage equal to one-half the input voltage so that amplifier 400 provides a zero or negative output when field effect transistor is conducting. When flip flop 64 is toggled to the set state, by peak detector 68, the logic level 1 signal from output 66 causes transistor 412 to turn on, thereby removing the positive DC voltage from the gate of field effect transistor 398 causing the field effect transistor to effectively open leaving capacitor 404 charged with a voltage equal to one-fourth the peak value of the input pulse. Amplifier 400 continues to provide a zero or negative output, while the trailing edge of the input pulse decreases until the half-peak value is reached at which time the inverting input of amplifier 400 receives a voltage equal to the voltage stored on capacitor 404 which is equal to one-fourth the peak voltage. The output of amplifier 400 abruptly changes state to positive level signal indicating that the half-pulse peak has been reached. This output then resets flip flop 64, turning off the charging current to capacitor 82.

The invention as described heretofore provides a blood cell counter for an on-line operation, wherein the counter provides a blood cell count readout corresponding to the blood cell count of the blood sample instantaneously passing through the aperture.

In a second embodiment of the present invention, wherein the blood cell counter is designed for use with individual blood samples, the electrode housing 2 receives a reservoir bottle 4 containing an individual blood sample 6.

The schematic diagram shown in FIG. 2, is modified as shown by the dotted portions of FIG. 2. A count period timer 90 has an output 92 which normally provides a logic level 1 signal and is connected to a diode 60d of the OR gate 60. The logic level 1 signal holds the flip flop 64 in the reset state, thereby disabling the flip flop. Count period timer has an input 94 connected to a 28 volt DC source through a normally open switch 96. Switch 96 is closed to initiate a count period and in response to the closing of switch 96, timer 90 provides a negative or logic level 0 output signal for a precisely repeatable count period of approximately 10 seconds. During this count period, the logic level 1 signal is removed from the reset input of flip flop 64 so that the peak detector output signal may drive flip flop 64 into the set state when a proper level pulse is detected. Flip Flop 64 remains in the set state until the trailing edge of the pulse decreases to a level equal to one-half of the pulse peak as previously described. After the count period has terminated, the output 92 of count period timer 90 again provides a logic level 1 signal thereby disabling flip flop 64. Thus, flip flop 64 may only be toggled to the set state during the precisely repeatable count period and the capacitor 82 may only accumulate charges during this count period.

The circuit diagram of FIG. 2 is further modified in that discharge path 84 comprises a resistor and a normally open switch connected in series between the anode of diode 80 and ground. Thus, in this embodiment capacitor 82 does not have a discharge path and the analog voltage developed on capacitor 82 during the count period corresponds to the blood cell count of the blood sample being tested. After the count period has terminated the meter provides an indication of the blood cell count of the tested sample. Prior to initiation of a subsequent blood cell count, the switch in discharge path 84 must be closed to discharge capacitor 82 through the resistor connected in series with the switch. Upon initial calibration of meter 36, an assayed blood sample is passed through the blood cell counter and the meter reading is adjusted to the assay value. Thus, the meter is calibrated to a known blood cell count and will remain calibrated for subsequent blood counts of unknown value.

Figure 5A:
FIG. 5 shows a comparison of the pulse widths at two different flow rates.
Figure 5B:
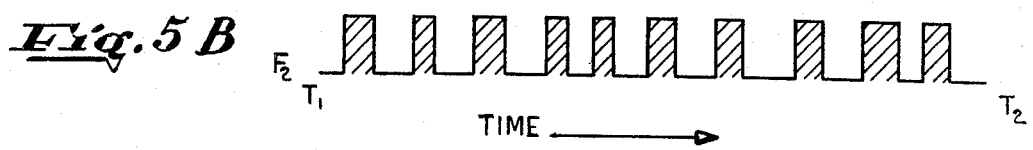

Thus, the present invention provides a blood cell counter that is rendered truly volume and flow rate independent by the unique use of integrating techniques as illustrated in FIG. 5. Referring to FIG. 5a, there is shown a series of current pulses provided to capacitor 82 resulting from blood cells passing through the aperture at a flow rate F1 between the time periods T1 and T2 which could represent the count period. In accordance with known principles, a capacitor may be charged with these current pulses to develop a voltage corresponding to the total area under the curve as illustrated by the sectioned pulses. Referring now to FIG. 5b, there is shown a series of current pulses corresponding to blood cells passing through the aperture at a flow rate of F2 equal to twice the flow rate F1 during the count period between T1 and T2. It will be noted that the pulses have decreased in width to one-half the original width, but that twice the number of blood cells have passed through the aperture and thus, twice the number of pulses have been provided. It is clear that the area under the curve of FIG. 5b is substantially equal to the area under the curve of FIG. 5a and that a capacitor would be charged to an equal voltage by the pulses of FIG. 5a and the pulses of FIG. 5b. The current pulses are all of the same amplitude since they originate from a constant current source. Thus, the present invention provides a blood cell counter that is truly volume and flow rate independent.

The blood cell counter of the present invention is less expensive than those heretofore provided and is of considerably smaller size so as to be available for use in small laboratories and doctors' offices. The blood cell counter accounts for partially coincident blood cells by the use of dynamically controlled threshold levels so that the capacitor is charged for a longer period of time when cells are in partial coincidence. Compensation for truly coincident blood cells is automatically introduced into the blood cell counter through the calibration of the meter to provide an output including the compensation. The invention also includes a pulse width limiter for reducing the errors introduced by bubbles passing through the aperture and a clog alarm for providing a warning if the aperture becomes clogged.

What is claimed is:

1. A method for counting the number of particles per unit volume suspended in a fluid medium having a conductivity different than the particles, comprising the steps of:

passing the fluid through an aperture;
applying an electronic signal across the aperture;
detecting changes in the signal level caused by the passage of particles through the aperture and forming pulses corresponding to the changes in the signal level;
detecting when the pulses exceed a predetermined threshold level; and
charging a capacitor at a known rate during a portion of each pulse that exceeds the predetermined threshold level, to develop a voltage on the capacitor corresponding to the number of particles per unit volume of the fluid medium, said voltage being independent of flow rate and the volume of fluid passed through the aperture.

2. A method as described in claim 1, wherein the step of charging a capacitor during a portion of each pulse includes the steps of:
detecting when the pulse peak occurs;
detecting when the trailing edge of each pulse decreases to a level equal to a predetermined fraction of the peak level of the pulse; and
charging the capacitor at a known rate during the interval between detection of the pulse peak and detection of the predetermined fraction of the pulse peak level of the trailing edge.

3. A method as described in claim 2, wherein the trailing edge is detected when it decreases to a level equal to one-half of the peak level of the pulse.

4. A method as described in claim 1, additionally including the steps of:
allowing the capacitor to charge only during a specified count period of known duration; and
measuring the voltage developed on the capacitor after the specified count period, said voltage corresponding to the number of particles per unit volume of fluid medium passing through the aperture.

5. A method as described in claim 4, additionally comprising the step of discharging the capacitor prior to commencement of a count period.

6. A method as described in claim 1, additionally comprising the step of continuously discharging the capacitor at a known rate so that the capacitor voltage corresponds to the number of particles per unit volume of fluid medium being passed through the aperture.

7. An instrument for counting the number of particles per unit volume suspended in a fluid medium, said fluid medium having a conductivity different from the particles, comprising:
an aperture;
means for passing the fluid medium through the aperture;
means for applying an electronic signal across the aperture;
means for detecting for detecting changes in the electronic signal level across the aperture and for forming pulses corresponding to the changes which result from changes in impedance across the aperture as the particles pass through the aperture
a storage capacitor; and
means responsive to the pulses for charging said storage capacitor at a predetermined constant rate during a portion of each pulse so that the capacitor develops an analog voltage corresponding to the number of particles per unit volume in the fluid medium.

8. An instrument as described in claim 7, additionally comprising means for continuously discharging said capacitor so that the voltage formed on said capacitor corresponds to the number of particles per unit volume of the fluid passing through the aperture.

9. An instrument as described in claim 7, additionally comprising timer means for allowing the capacitor to charge only during a specified count period.

10. An instrument as described in claim 7, wherein the last mentioned means comprises:
a constant current source; and
gate means for connecting the constant current source to the storage capacitor in response to the pulses so that the capacitor is charged only when particles are passing through the aperture.

11. An instrument as described in claim 7, additionally comprising detector means for detecting the pulse peaks and when the trailing edges of the pulses decline to a level equal to a specified fraction of the pulse peak and for providing an output signal during the interval between the detection of the pulse peak and the detection of the specified fraction of the pulse peak, the capacitor charging means being responsive to the output signal so that the capacitor is charged during the specified portion of each pulse.

12. An instrument for counting the number of particles per unit volume suspended in a fluid medium, said fluid having a conductivity different than the particles, comprising:
an aperture;
means for passing the fluid through the aperture;
means for applying an electronic signal across the aperture;
means for detecting modulation of the electronic signal across the aperture and for forming pulses corresponding to the modulation which results from a change in resistance across the aperture as particles pass through the aperture;
a storage capacitor;
means for charging said storage capacitor at a predetermined constant rate;
gating means for allowing the capacitor to be charged by the charging means; and
gate control means responsive to the pulses from the detecting means for controlling the gating means so that the capacitor is charged only when particles pass through the aperture, said gate controlling means comprising:
a threshold detector responsive to the pulses and having an output for normally providing a first level signal and a second level signal when the pulses exceed a specified threshold level;
a peak detector responsive to the pulses and having an output normally providing a first level signal and a second level signal when a pulse peak is detected;
a trailing edge detector responsive to the pulses and having an output normally providing a second level signal and a first level signal when the trailing edge of a pulse decreases to a level equal to a specified portion of the peak level of the pulse; and
a flip flop having a first input connected to the output of the threshold detector and the trailing edge detector and responsive to a first level signal from either the threshold detector or the trailing edge detector to hold the flip flop in a first state, and a second input connected to the output of the peak detector and responsive to the second level signal therefrom for driving the flip flop to a second state, the flip flop having an output connected to the gating means for controlling the gating means and allowing the capacitor to charge when the flip flop is in the second state, whereby the capacitor charges between the occurrence of a pulse peak and when the trailing edge declines to a level equal to the specified portion of the pulse peak.

13. An instrument as described in claim 12, additionally comprising a count period timer having an output normally providing a first level signal and a second level signal during a count period, the first input of the flip flop being connected to the output of the count period timer, the flip flop being responsive to the first level signal from the count period timer to hold the flip flop in the first state and preventing the flip flop from toggling to a second state.

14. An instrument as described in claim 12, wherein the trailing edge detector comprises:
   means responsive to the pulses for providing a signal corresponding to the specified portion of the instantaneous level of the pulses;
   a capacitor;
   gating means connecting the capacitor to the pulse responsive means so that the capacitor voltage equals the specified portion of the instantaneous level of the pulses, said gating means having an input connected to and responsive to the flip flop output for opening the connection between the capacitor and the pulse responsive means when the flip flop toggles to the second state upon detection of a pulse peak, whereby the capacitor stores a voltage corresponding to the specified portion of the pulse peak level;
   means for providing a signal corresponding to the instantaneous pulse level; and
   comparator means responsive to the signal for the last mentioned means and responsive to the capacitor voltage for providing a signal when the capacitor voltage exceeds the voltage level of the signal from the last mentioned means 15. A method for measuring particle concentration in a fluid suspension of particles, said method including the steps of: passing the particles in said suspension through a sensing zone having regions of indefinite response which regions are large with respect to a region of definite response in the sensing zone; sensing each particle as it passes through the sensing zone; and producing, in response to each particle sensed, an electrical particle pulse which, due to the different response regions in the sensing zone, has no well defined ends but has a well defined middle portion; ascertaining two geometrically defined points on the waveform of each particle pulse in the middle portion of the pulse, the points being spaced apart time-wise; measuring the duration of the segment of each particle pulse defined between the two points; and averaging the durations with respect to time to obtain a signal which is indicative of the concentration of particles in said fluid suspension.

16. The method according to claim 15 wherein the two ascertainable points comprise the peak of each particle pulse and a defined point on one of its leading or trailing edges.

17. The method according to claim 16 wherein said defined point is a point on the trailing edge and is at an instantaneous value which is a predetermined fractional value of the maximum ampltiude of the pulse.

18. Apparatus for measuring particle concentration in a fluid suspension of particles, said apparatus comprising: a particle analyzing device having a sensing zone, means for passing the particles in suspension through said sensing zone, means for sensing the presence of the particles within the influence of the zone and for producing in response to each particle sensed, an electrial particle pulse, said sensing zone having a dimension along the direction of movement of the particles such that the indefinite response regions at the beginning and end of said sensing zone are large compared to the definite response region in the center of said sensing zone, whereby said electrical particle pulses produced have no well-defined ends but have well-defined middle portions, first electrical circuit means for ascertaining two points on the waveform of each particle pulse in the middle portion of the waveform, said points being geometrically defined and spaced apart time-wise second electrical circuit means for measuring the duration of the segment of each particle pulse defined between said ascertainable points and for producing a duration-measuring pulse for each particle pulse, the duration of each duration-measuring pulse being that of said pulse segment and the amplitude thereof being the same for all duration-measuring pulses, and third electrical circuit means for averaging said duration-measuring pulses with respect to time to obtain a signal which is indicative of the concentration of particles in the fluid suspension.

19. The apparatus according to claim 18 wherein said third electrical circuit means includes circuit means for integrating said duration-measuring pulses with respect to time.

20. The apparatus according to claim 18 wherein said first circuit means is operable to ascertain for each particle pulse two points comprising a first point at the peak of the particle pulse and a second defined point on either the leading or trailing edge of the particle pulse.

21. The apparatus according to claim 20 wherein said first circuit means is operable to ascertain said defined point on the trailing edge of the particle pulse, said defined point being at an instantaneous value which is a predetermined fractional value of the maximum amplitude of the particle pulse.

22. The apparatus according to claim 18 wherein said second electrical circuit means is operable to generate for each particle pulse a rectangular duration-measuring pulse having a given amplitude and a duration equal to the time period between said two ascertainable points.

23. The apparatus according to claim 18 wherein said particle analyzing device is a Coulter type particle analyzing device and said sensing zone incudes a Coulter aperture.

* * * * *